US005344463A

United States Patent [19]
Chan et al.

[11] Patent Number: 5,344,463
[45] Date of Patent: Sep. 6, 1994

[54] HAIR DYE COMPOSITIONS AND METHODS UTILIZING 2-SUBSTITUTED-1-NAPHTHOL COUPLERS

[75] Inventors: Alexander Chan, Mineola, N.Y.; Yuh-Guo Pan, Stamford, Conn.; Mu-Ill Lim, Trumbell, Conn.; Richard Demarco, Danbury, Conn.

[73] Assignee: Clairol, Inc., New York, N.Y.

[21] Appl. No.: 61,517

[22] Filed: May 17, 1993

[51] Int. Cl.$^5$ ................................. A61K 7/13
[52] U.S. Cl. ........................................ 8/408; 8/405; 8/406; 8/410; 8/412; 8/423
[58] Field of Search ................... 8/406, 424, 649, 405, 8/408, 409, 410, 412, 423; 568/735

[56] References Cited

U.S. PATENT DOCUMENTS 3,960,476  6/1976  Ghilardi et al. ..................... 8/411
4,725,282  2/1988  Hoch et al. ......................... 8/405
4,754,069  6/1988  Braun et al. ........................ 8/410

FOREIGN PATENT DOCUMENTS 504663  9/1992  European Pat. Off. .

Primary Examiner—Paul Lieberman
Assistant Examiner—Caroline L. Dusheck
Attorney, Agent, or Firm—Morton S. Simon

[57] ABSTRACT

2-substituted-1-naphthols when coupled with an oxidation dye precursor in an oxidative dye system produce a long lasting intense color to hair. Use of such couplers makes available to the colorist novel oxidation hair dyes which surprisingly show a color shift to the red. Dyestuffs prepared through use of the 2-substituted-1-naphthol couplers are substantially more acid-fast compared to like dyestuffs using a 1-naphthol coupler. Compositions and a method of dyeing hair are also disclosed.

14 Claims, No Drawings

HAIR DYE COMPOSITIONS AND METHODS UTILIZING 2-SUBSTITUTED-1-NAPHTHOL COUPLERS

BACKGROUND OF INVENTION

Three classes of components are important in oxidative hair dyeing: oxidation dye precursors, oxidants, and couplers.

The oxidation dye precursor can be a primary intermediate such as a difunctional benzene derivative capable of being oxidized with resultant development of color, e.g. ortho- and para-phenylenediamines and para-aminophenols, or a hydroxyindole such as 5,6-dihydroxyindole.

Hydrogen peroxide is the usual oxidant, although persalts of various acids or solid organic peroxide adducts may be employed, especially where a solid oxidant is desired.

The third component type-the coupler-is important in hair coloring to produce color nuances necessary for the simulation of a natural hair color.

It is well known that the shade or color produced by a color coupler depends on its chemical nature.

The production of red shades has always been a problem in the development of lines of oxidative hair colorants. This was due to the absence of true "red couplers" among the various dye precursors. The problem was first overcome by the use of direct dyes in admixture with the oxidative dye precursors. In particular, 2,5-diaminonitrobenzene was widely used for this purpose. Moreover, the red direct dyes exhibit very poor wash fastness particularly on hair which had been previously subjected to permanent waving or relaxing. In consequence, the red shades so produced rapidly become drab brown after as little as one or two shampooings.

An attempt to improve the lastingness of red shades was the subject of U.S. Pat. No. 3,210,252 which disclosed the use of p-aminophenol and 5-amino-2-methylphenol and of U.S. Pat. No. 4,065,255 directed to the use of p-aminophenol and 5-($\beta$-hydroxyethyl) amino-2-methylphenol to produce red shades by an oxidative method. While these couples represent an improvement over the use of direct dyes, they still suffer from less than optimal light and wash fastness in oxidative dye compositions.

Furthermore, these couples produce an orange-red when coupled with p-aminophenol and a magenta when coupled with p-phenylenediamine and, when used in combination with both p-aminophenol and p-phenylenediamine, a dull hue is obtained.

Moreover, in alkaline dyeing formulations the couples are actually a vivid violet color due to ionization of the phenolic group. It is only after shampooing and the consequent drop in pH that the red color is evident. This has a very disconcerting effect on the dye user, as evidenced by calls to the manufacturers from consumers and hairdressers.

A second method to produce red shades involves the coupling of 1-naphthol and p-aminophenols as disclosed in U.S. Pat. Nos. 4,169,703, 4,997,451 and 5,047,066. This coupler is typically used to produce strong blue colors by coupling with p-phenylenediamines (U.S. Pat. No. 3,970,423). The red color produced is a weak orange-red as disclosed in the above patents and it is only poorly stable to light and shampooing. In view of these problems, it is not widely used.

The present inventors have surprisingly found that, when reacted with an oxidation dye precursor in the presence of a suitable oxidant, 2-substituted-1-naphthols of the general formula I

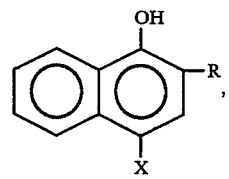

or salts thereof, preferably the sodium salt, wherein R is $C_1$–$C_6$ alkyl, hydroxy $C_1$–$C_6$ alkyl, amino $C_1$–$C_6$ alkyl wherein the amino group is substituted by $R^1$ and $R^2$, $R^1$ and $R^2$ being independently selected from the group consisting of hydrogen, $C_1$–$C_6$ alkyl, hydroxy $C_1$–$C_6$ alkyl, or $R^1$ and $R^2$ taken together with the nitrogen atom to which they are attached forming a 5 or 6 membered saturated ring, or an olefinic group selected from the group consisting of ethylene, propylene and butylene, and X is hydrogen or halogen (preferably chlorine or bromine) surprisingly impart a long lasting intense cosmetically desirable red color to hair. Although the color intensity gradually decreases upon repeated shampooing of the dyed hair, the color tones are advantageously maintained.

Another surprising advantage of these couplers over the prior art couplers is that the dye bath color is identical to the color that will be produced on the hair. There is no color shift as a result of rinsing out the formulation and subsequent shampooing.

Human perspiration generally has a pH of about 5 to 6. Perspiration emanating from the scalp is acidic. Because of acid rain, water supplies are becoming more acidic. An acidic environment can adversely affect dyestuffs that are not acid-resistant. Surprisingly, and advantageously, dyestuffs prepared through use of the 2-substituted-1-naphthol couplers of the present invention are substantially more acid-resistant than dyestuffs prepared through use of the 1-naphthol coupler.

OBJECTS OF THE INVENTION

It is an object of the present invention to provide new oxidation dyes for permanently dyeing keratin fibers, such as human hair. Such new oxidation dyes employ, as a coupler, 2-substituted-1-naphthols of the formula I.

It is a further object of the present invention to provide a new use for 2-substituted-1-naphthols of the formula I as a coupler in oxidative dyes for permanently dyeing keratin fibers such as human hair.

It is still a further object of the present invention to provide novel oxidative dye compositions for permanently dyeing keratin fibers such as human hair, such compositions employing an oxidation dye precursor and a 2-substituted-1-naphthol of formula I, as a coupler component.

These and other benefits and advantages of the present invention are disclosed more fully in the detailed description of the invention a summary of which follows.

DETAILED DESCRIPTION OF THE INVENTION

The 1-naphthol compounds (I) of the present invention, or salts thereof, are quite suitable for use generally as dye couplers in oxidative dye compositions. The oxidative dye composition further contains an oxidation dye precursor such as a primary intermediate, e.g. p-phenylenediamine, or a hydroxyindole, e.g. 5,6-dihydroxyindole, the composition being oxidizable with hydrogen peroxide or other oxidant to produce an array of colors.

It is particularly surprising that when a compound of formula I is coupled with a p-aminophenol derivative, the color imparted to hair is much redder than when 1-naphthol is coupled with the same p-aminophenol derivative. The bright red colors obtained when couplers of formula I are coupled with a p-amino-phenol derivative are not achievable by the current state of the art.

In a particular useful and preferred aspect of the present invention, it has been found that certain of the 2-substituted-1-naphthol couplers (I) and their salts, when employed in an alkaline oxidizing medium with a suitable oxidation dye precursor such as a primary intermediate, especially p-aminophenol primary intermediates, unexpectedly impart to the keratin fibers a brighter red shade. Moreover, it has also been found that surprisingly long-lasting shades are obtainable, which resist fading caused by weathering and/or light. In this regard, they are more long-lasting than the red shades obtained when 1-naphthol is employed as the coupler. The bright red shades produced by the couplers (I) when employed with p-aminophenols are particularly important to achieve a true auburn hair color having a realistic tonal impression.

It should be understood that the red colors referred to herein are the actual hues obtained when the hair is dyed with the coupler (I) as the only coupler and a suitable primary intermediate, i.e., a primary intermediate used in connection with this preferred aspect of the invention (such as p-amino-phenol), that provides with coupler (I) bright red color to the hair fiber. The suitable primary intermediate may be easily determined by actual testing with the couplers (I) of the present invention, in accordance with the procedures outlined in the examples.

Particularly preferred couplers in this preferred aspect of the invention are:

2-methyl-1-naphthol,
2-ethyl-1-naphthol,
2-propyl-1-naphthol,
2-hydroxymethyl-1-naphthol,
2-hydroxyethyl-1-naphthol,
and their salts, especially sodium salts.

The dye compositions of the present invention comprise from about 0.001 to about 10%, preferably from 0.01 to about 5%, most preferably from about 0.05 to about 2.5%, of a coupler, all or part of which coupler may be the coupler (I), from about 0.001 to about 10%, preferably from about 0.05 to about 5%, most preferably from about 0.2 to about 2.5%, of an oxidation dye precursor, such as a primary intermediate or an hydroxyindole, and water. The proportions and amounts of the several constituents in the hair dye composition will depend on the nature and amount of the dye components, the tonal impression to be created, and the color of the hair to be dyed. Whether to use the coupler (I) alone or in combination with other couplers or whether to include two or more primary intermediates, will depend on the shade of the color desired. Generally, the coupler to primary intermediate molar ratio is from about 0.1:1 to about 10:1, preferably from about 1:1 to about 4:1.

The dye compositions of the present invention comprise the coupler (I) and, optionally, one or more additional coupler compounds, for example, m-phenylenediamines, such as 2,4-bis (2-hydroxyethoxy)-1,5-diaminobenzene and 2,4-diaminophenoxy-ethanol; m-amino-phenols, such as m-aminophenol, 5-amino-2-methylphenol, 5-(N-2-hydroxyethylamino)-2-methylphenol, 2-methyl-5-carbamyl-methylaminophenol and 5-amino-2,6-dimethylphenol; m-acetamidophenols, such as 5-acetamido-2-methylphenol; m-ureido-phenols; 1-naphthol; resorcinols; and heterocyclic couplers, such as 6-hydroxy-benzomorpholine, 2-6-diaminopyridine and 1-phenyl-3-methylpyrazolone.

The dye compositions of the instant invention contain at least one primary intermediate. Combinations of primary intermediates may be employed. Primary intermediates which can be utilized in the invention are well known to those skilled in the art.

The primary intermediates incorporated in the dye composition of the present invention are preferably:

(i) p-phenylenediamines, for example, dye compounds of the formula II

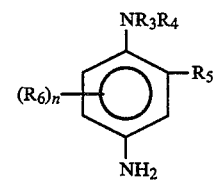

wherein $R_3$ and $R_4$ are substituent groups including hydrogen, alkyl, hydroxyalkyl, aminoalkyl, and acylaminoalkyl; $R_5$ is hydrogen, alkyl, alkoxy or halogen; $R_6$ is hydrogen, halogen, alkyl or alkoxy, and n is 1 or when $R_6$ is methyl n is one or two; each of the aforementioned alkyl moieties having from 1 to 6, preferably from 1 to 4 carbon atoms; compound (II) being in the form of the free base or in the form of an acid salt, such as the hydrochloride; a (ii) p-aminophenols, for example, dye compounds of the formula III

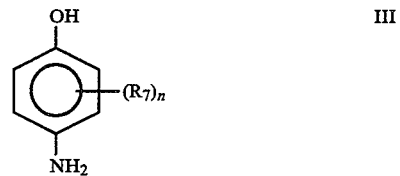

wherein $R_7$ is hydrogen, $C_1$–$C_6$ alkyl, hydroxy $C_1$–$C_6$ alkyl, $C_1$–$C_6$ alkoxy, $C_1$ carboxyl, or halogen, and n is one or when $R_7$ is methyl n is one or two.

(iii) 4-amino-1-naphthol or 4-[(2-acetamidoethyl-)amino]phenol; or (iv) mixtures thereof.

Illustrative compounds II include p-phenylenediamine; 2,6-dimethyl-3-methoxy-p-phenylenediamine dihydrochloride; 3-methoxy-4-amino-N,N-dimethylaniline sulfate; and N,N--bis(2-hydroxyethyl)-p-phenylenediamine sulfate.

Illustrative of the compounds of formula III are p-aminophenol; 4-amino-2,6-dimethylphenol; 5-aminosalicylic acid; 4-[(2-acetamidoethyl)-amino]phenol sulfate;

4-amino-2-methylphenol; 4-amino-3-methylphenol hydrochloride, and 2,5-dimethyl-4-aminophenol.

Particularly preferred primary intermediates include p-phenylenediamine, N,N-bis(2-hydroxyethyl)-p-phenylenediamine, p-aminophenol, p-amino-m-methylphenol, p-amino-o-methylphenol, 5-aminosalicylic acid, 2,5-diaminotoluene, and 4-amino-1-naphthol.

Most preferred primary intermediates include p-phenylenediamine, p-toluenediamine, p-aminophenol,4-amino-2-methylphenol, and N,N-bis(2-hydroxyethyl)-p-phenylenediamine sulfate.

Mixtures of primary intermediates of formula II and formula III may be employed. For example, two or more primary intermediate compounds (II) and (III) may be incorporated into the dye compositions of the present invention. The hair dye composition disclosed herein may also include, in addition to the primary intermediate compounds (II) and (III), one or more dyes such as anthraquinones, nitrobenzenes, diphenylamines, azo dyes, indoanilines, indophenols and indamines.

The dye compositions of the present invention include an aqueous, alcoholic or hydroalcoholic medium, as a vehicle or carrier. The alcohol moiety, if present, is usually a lower alkanol of from 1 to 6 carbons, especially ethanol or propanol, but may be a glycol having a total of up to 10 carbons, especially less than 6 carbons, such as propylene glycol, butyl glycol and diethyleneglycol monobutyl ether. The vehicle is generally from about 1 to 75% by weight of the composition. Typically, the alcohol moiety, if present, comprises about 10 to about 50% by weight of said vehicle, and the vehicle is typically from about 10 to about 50% by weight of the composition.

The compositions of the present invention may further include a cationic, anionic, nonionic or amphoteric surface-active agent in an amount of up to about 20% by weight, preferably from about 0.5 to about 10% by weight. Representative surface-active agents include octoxynol-1, nonoxynol-4, oleic acid and salts thereof, lauric acid and salts thereof, Merquat 100, polyquaternium 6, cocoamidopropylbetaine and sodium oleoamphopropionate.

The hair dye compositions of the present invention may also include one or more adjuvants such as perfumes; antioxidants, such as sodium sulfite and sodium thioglycolate; sequestering agents, such as EDTA; alkalizing agents, such as ammonia or an alkanolamine; and acidifying agents, such as oleic acid, acetic acid and phosphoric acid. These adjuvants are present in an amount effective to provide their functional activity. The pH of the compositions of the present invention ranges typically from about 8 to about 11.

Although it is preferred to admix the developer, e.g., hydrogen peroxide, and the dyeing composition at the moment of use, compositions containing hydrogen peroxide are within the scope of this invention. The hydrogen peroxide developer is typically an aqueous solution of $H_2O_2$ having a concentration between 5 and 50 volumes, preferably between 10 and 40 volumes.

Upon mixing with the developer, the primary intermediate is oxidized and thereafter reacts with the coupler to provide the intended color. After mixing, the mixture is applied to hair for typically from about 5 to about 60 minutes, especially between about 20 and about 45 minutes. As known in the art, the dye composition often contains more than one primary intermediate and more than one coupler, to provide the shade of hair color desired.

The invention is further described by way of the examples below.

It should be noted that, unless otherwise indicated, all percentages herein are percentage by weight, based on the total weight of the composition.

Moreover, unless otherwise indicated, the following general procedure is employed.

GENERAL PROCEDURE 5.0 g of test composition are mixed with 2.5 g of hydrogen peroxide solution (20 vol.). The resultant mixture is applied to piedmont hair and permitted to remain in contact with the hair for 30 minutes. The thus dyed hair is then shampooed and rinsed with water. Tristimulus values are then determined using a Hunter Tristimulus Colorimeter (Model D25M-9). The tristimulus a value is an indicator of the degree of greenness and redness. A larger a value indicates a redder color. A smaller a value indicates a greener color.

EXAMPLE 1

The following Comparative compositions A and B were prepared in accordance with the general procedure.

|  | A | B |
| --- | --- | --- |
| 1-naphthol | 0.58% | — |
| 2-methyl-1-naphthol | — | 0.64% |
| p-phenylenediamine | 0.43% | 0.43% |
| ethyl alcohol | 30.00% | 30.00% |
| ammonium hydroxide | qs pH 9 | qs pH 9 |
| water | qs 100% | qs 100% |

Composition A imparted a dark blue violet color to the hair. Composition B imparted a vivid violet color to the hair.

Tristimulus values, reported in Table 1 below, show that composition B (in accordance with the present invention) produced a swatch having a larger a value than that of the swatch dyed with composition A. Thus, use of 2-methyl-1-naphthol as a coupler produced a redder color than when 1-naphthol was used as the coupler.

TABLE 1

Tristimulus Values Dyed Swatches

| Composition | Primary Intermediate | Coupler | L | a | b |
| --- | --- | --- | --- | --- | --- |
| A | p-phenylenediamine | 1-naphthol | 14.5 | 3.6 | −3.7 |
| B | p-phenylenediamine | 2-methyl-1-naphthol | 14.0 | 5.4 | −3.6 |

EXAMPLE 2

The following comparative compositions C and D were prepared in accordance with the General Procedure.

|  | C | D |
| --- | --- | --- |
| 1-naphthol | 0.48% | — |
| 2-methyl-1-naphthol | — | 0.53% |
| N,N-bis(2-hydroxyethyl)-p-phenylenediamine sulfite | 0.97% | 0.97% |
| ethyl alcohol | 30.00% | 30.00% |
| sodium sulfite | 0.40% | 0.40% |
| ammonium hydroxide | qs pH 9 | qs pH 9 |

Composition C imparted a greenish blue color to the hair. Composition D colored the hair blue.

Tristimulus values are reported in Table 2 below.

As is evident from the results of Table 2, the swatch treated with composition D (a composition in accordance with the present invention) has a larger a value than the swatch treated with composition C. Thus the use of 2-methyl-1-naphthol as a coupler produced a redder color on hair than when 1-naphthol was used as the coupler.

TABLE 2

Tristimulus Values of Dyed Swatches

| Composition | Primary Intermediate | Coupler | L | a | b |
|---|---|---|---|---|---|
| C | N,N-bis (2-hydroxyethyl)-p-phenylenediamine | 1-naphthol | 20.3 | 3.4 | −20.4 |
| D | N,N-bis (2-hydroxyethyl)-p-phenylenediamine | 2-methyl-1-naphthol | 20.4 | 7.0 | −21.8 |

EXAMPLE 3

The following comparative compositions E and F were prepared in accordance with the General Procedure.

| | E | F |
|---|---|---|
| 1-naphthol | 0.40% | — |
| 2-methyl-1-naphthol | — | 0.44% |
| p-aminophenol | 0.30% | 0.30% |
| propylene glycol | 30.00% | 30.00% |
| sodium sulfite | 0.20% | 0.20% |
| ammonium hydroxide | qs pH 9 | qs pH 9 |
| water | qs 100% | qs 100% |

Composition E imparted a red-violet color to the hair. Composition F imparted a red color to the hair, without the violet hue obtained with composition E.

Tristimulus values are reported in Table 3 below:

TABLE 3

Tristimulus Values of Dyed Swatches

| Composition | Primary Intermediate | Coupler | L | a | b |
|---|---|---|---|---|---|
| A | P-aminophenol | 1-naphthol | 32.8 | 21.4 | 8.8 |
| B | P-aminophenol | 2-methyl-1-naphthol | 38.7 | 26.3 | 13.6 |

EXAMPLE 4

| | Compositions | | | | |
|---|---|---|---|---|---|
| | G | H | I | J | K |
| 2-propyl-1-naphthol | 0.53% | — | — | — | — |
| 2-dimethylaminomethyl-1-naphthol | — | 0.57% | — | — | — |
| 2-(β-propenyl)-1-naphthol | — | — | 0.53% | — | — |
| 2-methyl-1-naphthol | — | — | — | 0.44% | 0.44% |
| p-amino-m-methylphenol | — | — | 0.35% | — | — |
| p-amino-o-methylphenol sulfate | — | — | — | — | 0.97% |
| p-aminophenol | 0.30% | 0.30% | — | 0.35% | — |
| ethyl alcohol | 50.00% | 50.00% | 50.00% | 30.00% | 30.00% |
| ammonium hydroxide | qs pH 9 | qs pH 9 | qs pH 9 | qs pH 9 | qs pH 9 |
| water | qs 100% | qs 100% | qs 100% | qs 100% | qs 100% |

The above compositions G, H, I, J and K were prepared in accordance with the General Procedure Composition G dyed the hair an orange-red. Composition H dyed the hair a reddish-brown. Composition I dyed the hair a red-violet color. Composition J dyed the hair a deep red. Composition K dyed the hair a cherry red.

EXAMPLE 5

European patent application 345,728 indicates that 5-amino-salicylic acid and 1-naphthol produced a vivid reddish color on hair. Composition L (a composition in accordance with European Patent application 345,728) and composition M (a composition in accordance with the present invention) were prepared by the General Procedure.

| | L | M |
|---|---|---|
| 1-naphthol | 0.40% | — |
| 2-methyl-1-naphthol | — | 0.44% |
| 5-aminosalicylic acid | 0.45% | 0.45% |
| ethyl alcohol | 50.00% | 50.00% |
| ammonium hydroxide | qs pH 9 | qs pH 9 |
| water | qs 100% | qs 100% |

Tristimulus values of the dyed swatches are reported in Table 4, below. It was evident from the results reported in Table 4 and confirmed by visual observation that the use of 2-substituted-1-naphthol as a coupler afforded a red color whereas, contrary to the teaching of European patent application 345,728, when 1-naphthol was employed as the coupler, the resultant color was violet not red.

TABLE 4

Tristimulus Values of Dyed Swatches

| Composition | Primary Intermediate | Coupler | L | a | b |
|---|---|---|---|---|---|
| L | 5-aminosalicylic acid | 1-naphthol | 64.8 | 7.3 | 15.7 |
| M | 5-aminosalicylic acid | 2-methyl-1-naphthol | 63.2 | 10.8 | 16.7 |

EXAMPLE 6

To demonstrate that dyestuffs prepared through use of a 2-substituted-1-naphthol coupler of the present invention are more acid-resistant (in other words, more acid-fast) than dyestuffs prepared through use of the 1-naphthol coupler, the following test was conducted.

A tress of bleached hair was dyed with a combination of p-aminophenol and 2-methyl-1-naphthol. As a control, a like tress was dyed with a combination of p- aminophenol and 1-naphthol. Both dyed tresses were treated as follows:

The dyed tress was immersed for 3 hours, at a temperature of 50° C., in a solution having the following composition:

| sodium chloride | 1% (w/w) |
|---|---|
| lactic acid | 0.1% (w/w) |
| dibasic sodium phosphate | 0.1% (w/w) |
| histidine monohydrochloride | 00.25% (w/w) |
| deionized water | qs 100% |

Sufficient hydrochloric acid was added to adjust the pH to 3.5.

After such treatment with Tristimulus values of the treated tresses were determined. The results are reported below.

TABLE 5

| Tristimulus Values of Treated Tresses | | | |
|---|---|---|---|
| | L | a | b |
| Tress dyed using 2-methyl-1-naphthol as the coupler | | | |
| Initial Value | 28.4 | 24.2 | 11.8 |
| Final Value | 32.0 | 23.7 | 13.0 |
| Tress dyed using 1-naphthol as the coupler | | | |
| Initial Value | 26.7 | 19.0 | 7.7 |
| Final Value | 29.8 | 14.4 | 6.3 |

In considering the above results it should be noted that the less the ▲ a value the greater the acid-fastness of the dye. The results reported above show that the change in a value (▲ a) for the tress dyed with 2-methyl-1-naphthol employed as the coupler was 0.5 (24.2-23.7). While the change in a value (▲ a) for the tress dyed with 1-naphthol employed as the coupler was 4.6 (19.0-14.4). Thus, it is readily apparent that the use of 2-substituted-1-naphthol as the coupler, in accordance with present invention, resulted in a dyestuff more than 9 times more acid-fast that the dyestuff prepared through use of the 1-naphthol coupler of the prior art.

What is claimed is:

1. In an oxidative dye composition for dyeing a keratin fiber, the composition containing an oxidation dye precursor, a coupler, at least one material selected from the group consisting of perfumes, antioxidants, sequestering agents, alkalizing agents, acidifying agents and developers and a cosmetically acceptable vehicle, the precursor and the coupler being present in respective amounts such that when the precursor is activated it reacts with the coupler to produce a tinctorially effective amount of a dye compound, the improvement which comprises the coupler is a 2-substituted-1-naphthol compound having the formula I

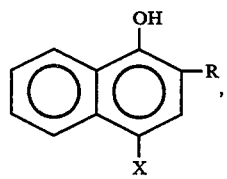

or a salt thereof, wherein R is $C_1$–$C_6$ alkyl, hydroxy $C_1$–$C_6$ alkyl, amino $C_1$–$C_6$ alkyl wherein the amino group is substituted by $R^1$ and $R^2$, $R^1$ and $R^2$ being independently selected from the group consisting of hydrogen, $C_1$–$C_6$ alkyl, hydroxy $C_1$–$C_6$ alkyl, or $R^1$ and $R^2$ taken together with the nitrogen atom to which they are attached forming a 5 or 6 membered saturated ring, or an olefinic group selected from the group consisting of ethylene, propylene and butylene, and X is hydrogen or halogen.

2. The composition according to claim 1, wherein the oxidation dye precursor is a primary intermediate and the compound of formula I is selected from the group consisting of 2-methyl-1-naphthol, 2-ethyl-1-naphthol, 2-propyl-1-naphthol, 2-hydroxymethyl-1-naphthol, 2-hydroxyethyl-1-naphthol, and salts thereof.

3. The composition according to claim 1, wherein the oxidation dye precursor is a primary intermediate selected from the group consisting of
(i) p-phenylenediamines having the formula II

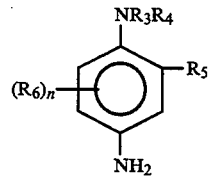

wherein $R_3$ and $R_4$ are, independently, hydrogen, $C_1$–$C_6$ alkyl, hydroxy $C_1$–$C_6$ alkyl, amino $C_1$–$C_6$ alkyl, or acylamino $C_1$–$C_6$ alkyl; $R_5$ is hydrogen, $C_1$–$C_6$ alkyl, $C_1$–$C_6$ alkoxy or halogen; $R_6$ is hydrogen, halogen, $C_1$–$C_6$ alkyl or $C_1$–$C_6$ alkoxy; and n is 1 or when $R_6$ is methyl n is 1 or 2 and acid addition salts thereof;

(ii) p-aminophenols of the formula III

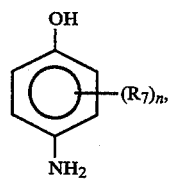

or a salt thereof, wherein $R_7$ is hydrogen, $C_1$–$C_6$ alkyl, hydroxy $C_1$–$C_6$ alkyl, $C_1$–$C_6$ alkoxy, $C_1$ carboxyl, or halogen, and n is 1 or when $R_7$ is methyl n is 1 or 2; and (iii) 4-amino-1naphthol or 4-[(2-acetamidoethyl-)amino]phenol, or (iv) mixtures thereof.

4. The composition according to claim 3, wherein the oxidation dye precursor is p-phenylenediamine, 2,6-dimethyl-3-methoxy-p-phenylenediamine dihydrochloride, 3-methoxy-4-amino-N,N-dimethylaniline sulfate or N,N-bis (2-hydroxyethyl)-p-phenylenediamine sulfate, p-aminophenol, 4-amino-2,6-dimethylphenol, 5-aminosalicylic acid, 4-[(2-acetamidoethyl)amino]-phenol sulfate, 4-amino-2-methylphenol, 4-amino-3-methylphenol hydrochloride or 2,5-dimethyl-4-aminophenol.

5. The composition according to claim 1, wherein the oxidation dye precursor is p-phenylenediamine, N,N-bis(2-hydroxyethyl)-p-phenylenediamine, p-aminophenol, p-amino-m-methylphenol, p-amino-o-methylphenol, 5-aminosalicylic acid, 2,5-diaminotoluene or 4-amino-1-naphthol.

6. The composition according to claim 1, wherein the oxidation dye precursor is p-phenylenediamine, p-toluenediamine, p-aminophenol, 4-amino-2-methylphenol or N,N-bis(2-hydroxyethyl)-p-phenylenediamine sulfate.

7. In a method for dyeing hair including the steps of activating an oxidation dye precursor, reacting the activated oxidation dye precursor with a coupler to produce a tinctorially effective amount of a hair dye and applying the hair dye to a hair fiber; the improvement which comprises the coupler is a 2-substituted-1-naphthol compound having the formula I

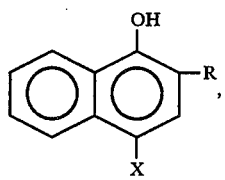

or a salt thereof, wherein R is $C_1$-$C_6$ alkyl, hydroxy $C_1$-$C_6$ alkyl, amino $C_1$-$C_6$ alkyl, wherein the amino group is substituted by $R^1$ and $R^2$, $R^1$ and $R^2$ being independently selected from the group consisting of hydrogen, hydroxy $C_1$-$C_6$ alkyl, or $R^1$ and $R^2$ taken together with the nitrogen atom to which they are attached forming a 5 or 6 membered saturated ring, or an olefinic group selected from the group consisting of ethylene, propylene and butylene, and X is hydrogen or halogen, whereby said hair fiber is imparted a coloration having increased resistance to shampooing.

8. The method, according to claim 7, wherein the oxidation dye precursor is a primary intermediate and the compound of formula I is selected from the group consisting of 2-methyl-1-naphthol, 2-ethyl-1-naphthol, 2-propyl-1-naphthol, 2-hydroxymethyl-1-naphthol, 2-hydroxyethyl-1naphthol, and salts thereof.

9. The method, according to claim 7, wherein the oxidation dye precursor is a primary intermediate selected from the group consisting of (i) p-phenylenediamines having the formula II

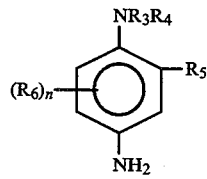

wherein $R_3$ and $R_4$ are, independently, hydrogen, $C_1$-$C_6$ alkyl, hydroxy $C_1$-$C_6$ alkyl, amino $C_1$-$C_6$ alkyl, or acylamino $C_1$-$C_6$ alkyl; $R_5$ is hydrogen, $C_1$-$C_6$ alkyl, $C_1$-$C_6$ alkoxy or halogen; $R_6$ is hydrogen, halogen, $C_1$-$C_6$ alkyl or $C_1$-$C_6$ alkoxy and n is 1 or when $R_6$ is methyl n is 1 or 2; and acid addition salts thereof; (ii) p-aminophenols of the formula III

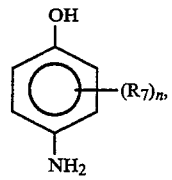

or a salt thereof, wherein $R_7$ is hydrogen, $C_1$-$C_6$ alkyl, hydroxy $C_1$-$C_6$ alkyl, $C_1$-$C_6$ alkoxy, $C_1$ carbonyl, or halogen, and n is 1 or when $R_7$ is methyl n is 1 or 2; and (iii) 4-amino-1-naphthol or 4-[(2-acetamidoethyl)amino]phenol; and (iv) mixtures thereof.

10. The method according to claim 9, wherein the oxidation precursor is p-phenylenediamine, 2,6-dimethyl-3-methoxy-p-phenylenediamine dihydrochloride, 3-methoxy-4-amino-N,N-dimethylaniline sulfate or N,N-bis (2-hydroxyethyl)-p-phenylenediamine sulfate, p-aminophenol, 4-amino-2, 6-dimethylphenol, 5-aminosalicylic acid, 4[(2-acetamidoethyl)amino]phenol sulfate, 4-amino-2-methylphenol, 4-amino-3-methylphenolhydrochloride or 2,5-dimethyl-4-aminophenol.

11. The method according to claim 7, wherein the oxidation dye precursor is p-phenylenediamine, N,N-bis(2-hydroxyethyl)-p-phenylenediamine, p-aminophenol, p-amino-m-methylphenol, p-amino-o-methylphenol, 5-aminosalicylic acid, 2,5-diaminotoluene, or 4-amino-1-naphthol.

12. The method according to claim 7, wherein the oxidation dye precursor is p-phenylenediamine, p-toluenediamine, p-amino-phenol, 4-amino-2methylphenol or N,N-bis(2-hydroxyethyl)-p-phenylenediamine sulfate.

13. The composition according to claim 5, wherein the oxidation dye precursor is p-amino-o-methyl phenol and the coupler of formula I is 2-methyl-1-naphthol.

14. The method according to claim 11, wherein the oxidation dye precursor is p-amino-o-methyl phenol and the coupler of formula I is 2-methyl-1-naphthol.

* * * * *